United States Patent [19]
Gordon et al.

[11] Patent Number: 5,977,039
[45] Date of Patent: *Nov. 2, 1999

[54] PERSONAL CLEANSING SYSTEM COMPRISING A PERSONAL CLEANSING IMPLEMENT AND A LIQUID CLEANSER WITH MOISTURIZER

[75] Inventors: Gail Gordon, Cincinnati, Ohio; Cheryl Oram Schoenberg, Niceville, Fla.; Lisa Catherine Winder, Cincinnati, Ohio; Gene Michael Altonen, West Chester, Ohio; Andrew Raymond Cipra, Blue Ash, Ohio

[73] Assignee: The Procter & Gamble Company, Cincinnati, Ohio

[*] Notice: This patent is subject to a terminal disclaimer.

[21] Appl. No.: 08/878,188

[22] Filed: Jun. 18, 1997

Related U.S. Application Data

[63] Continuation-in-part of application No. 08/226,451, Apr. 21, 1994, abandoned.

[51] Int. Cl.⁶ .............................. C11D 3/16; C11D 17/04
[52] U.S. Cl. ................... 510/130; 510/135; 510/137; 510/155; 510/159; 510/406; 510/417; 510/427; 510/437; 510/466
[58] Field of Search ................... 510/130, 137, 510/155, 135, 159, 295, 406, 417, 427, 466, 120

[56] References Cited

U.S. PATENT DOCUMENTS

| | | | |
|---|---|---|---|
| Re. 34,584 | 4/1994 | Grote et al. | 252/142 |
| 2,581,779 | 1/1952 | Abraham | 15/209 |
| 3,281,884 | 11/1966 | Feil | 15/244 |
| 3,345,668 | 10/1967 | Windsor | 15/209 |
| 4,196,134 | 4/1980 | Ball et al. | 260/404.8 |
| 4,199,835 | 4/1980 | Heyer et al. | 15/207 |
| 4,329,334 | 5/1982 | Su et al. | 424/70 |
| 4,376,789 | 3/1983 | Lowicki et al. | 424/361 |
| 4,462,135 | 7/1984 | Sanford | 15/105 |
| 4,490,355 | 12/1984 | Desai | 424/70 |
| 4,551,330 | 11/1985 | Wagman et al. | 424/59 |
| 4,578,216 | 3/1986 | Fujii et al. | 252/542 |
| 4,673,525 | 6/1987 | Small et al. | 252/132 |
| 4,740,367 | 4/1988 | Force et al. | 424/47 |
| 5,002,680 | 3/1991 | Schmidt et al. | 252/90 |
| 5,076,953 | 12/1991 | Jordan et al. | 252/108 |
| 5,085,857 | 2/1992 | Reid et al. | 424/70 |
| 5,096,608 | 3/1992 | Small et al. | 252/132 |
| 5,132,037 | 7/1992 | Greene et al. | 252/108 |
| 5,144,744 | 9/1992 | Campagnoli | 29/446 |
| 5,154,849 | 10/1992 | Visscher et al. | 252/174.15 |
| 5,234,619 | 8/1993 | Greene et al. | 252/108 |
| 5,295,280 | 3/1994 | Hudson et al. | 15/222 |
| 5,308,526 | 5/1994 | Dias et al. | 252/125 |
| 5,312,559 | 5/1994 | Kacher et al. | 252/125 |
| 5,409,640 | 4/1995 | Giret et al. | 252/546 |
| 5,412,830 | 5/1995 | Girardot et al. | 15/118 |
| 5,439,682 | 8/1995 | Wivell et al. | 724/401 |
| 5,518,647 | 5/1996 | Zocchi | 510/159 |
| 5,607,678 | 3/1997 | Moore et al. | 424/401 |
| 5,632,978 | 5/1997 | Moore et al. | 510/159 |
| 5,650,384 | 7/1997 | Gordon et al. | 510/159 |
| 5,713,094 | 2/1998 | Markey et al. | 15/229.11 |
| 5,720,961 | 2/1998 | Fowler et al. | 424/401 |

FOREIGN PATENT DOCUMENTS

| | | | |
|---|---|---|---|
| 047797 | 3/1982 | European Pat. Off. | |
| 46686 | 3/1982 | European Pat. Off. | |
| 250 181 A2 | 12/1987 | European Pat. Off. | C11D 1/94 |
| 10198 | 8/1912 | United Kingdom | |
| 9206669 | 4/1992 | WIPO | |
| WO 93/21293 | 10/1993 | WIPO | C11D 1/88 |

OTHER PUBLICATIONS

Jergens Refreshing Body Shampoo Product Statement, ©1992 The Andrew Jergens Company (Photograph included).

Rainbath Refreshing Shower and Bath Gel Product Statement, ©Neutrogena Corp. (Photograph included) (Pre–May 1993).

H₂O Facial Sponge, 1989.

The Bodykiss Bath Sponge, 1991.

Journal of Investigative Dermatology, T. J. Franz, 1975, 64, pp. 190–195.

*Primary Examiner*—Lorna Douyon
*Attorney, Agent, or Firm*—Darryl C. Little; Tara M. Rosnell; George W. Allen

[57] ABSTRACT

A system for cleansing the skin comprises a hydro-phobic diamond-mesh sponge and a liquid cleansing and moisturizing composition with excellent lather in the same washing and rinsing operation. The system provides improved lather and overall acceptability for mild liquid cleansing compositions which contain moisturizers and especially for those which would otherwise have marginal lather.

36 Claims, 1 Drawing Sheet

PERSONAL CLEANSING SYSTEM COMPRISING A PERSONAL CLEANSING IMPLEMENT AND A LIQUID CLEANSER WITH MOISTURIZER

This is a continuation-in-part of application Ser. No. 08/226,451, filed on Apr. 21, 1994, now abandoned.

TECHNICAL FIELD

This invention relates to a kit comprising a personal cleansing implement and a personal liquid cleanser for bath or shower.

BACKGROUND OF THE INVENTION

A variety of cleansing systems have been used to remove dirt and dead skin from the body and moisturize the cleansed skin. Such systems include the use of moisturizing lotion after the use of a soap or surfactant in combination with a cleaning instrument such as terry wash clothes, soft and brittle, and various cleaning pads, scouring pads, natural and synthetic sponges, etc.

Prior art cleaning and moisturizing personal cleansing kits have some disadvantages which have limited their effectiveness in personal skin care. Many cleansers, for example, are in fact harsh. Most do not contain an effective amount of a moisturizer. Many mild liquid cleansers traditionally do not lather well. Likewise, some cleaning instruments do not lather well when used with liquid cleansers. This is particularly so when milder liquid cleansers are used. Other cleansing instruments become water logged. Some make it difficult to remove the water containing the removed dirt from the instrument. Some impede lather; which is especially true for liquid cleansing and moisturizing cleansers. Yet other instruments absorb the oil conditioner in cleansing and moisturizing products. Others retain the water and often develop unpleasant odors, as well as become a place for breeding of bacteria, germs, mold, etc. Yet other instruments absorb the oil conditioner in cleansing and moisturizing products and thereby compete with the skin.

In addition, many of the instruments have very low strength and are easily destroyed after they have been used several times.

The need for mild skin cleansing system is made more acute by the need to wash more often to reduce body odors in city crowds and by the aging of the human population and the ever-increasing environmental insult to which the skin is subject. The mildest skin cleansing products can, at best, produce cleansing without negatively affecting the skin condition. To achieve an improvement in skin condition, the consumer is forced to use a second, separate product often called a "moisturizer". The use of two separate products to achieve the desired skin state is inconvenient and often unpleasant due to the greasy skin feel resultant from many moisturizers. As a result, many persons suffer from the effects of poor skin condition rather than use two separate products.

There is a clear need for a system which is capable of delivering both mild skin cleansing and a skin conditioning benefit; since most people don't use a moisturizer daily. Some skin cleansing products contain humectant substances which, although effective in topical application, are ineffective in cleansing products. These humectants are ineffective because they are very water soluble and suffer from poor skin substantivity. Hydrophobic emollient materials are generally more substantive to the skin, but are more difficult to incorporate into an aqueous skin cleansing matrix and/or are absorbed into traditional cleansing instruments. There are also at least two other sources of difficulty typically encountered with such liquid cleansers: poor lather effects and physically unstable product.

The present invention allows for the use of a selected personal cleansing implement with a lathering cleansing and moisturizing liquid cleanser containing an effective amount of a hydrophilic, oily or hydrophobic moisturizer and mixtures thereof.

The present invention allows for the use of higher levels of humectants in a "cleansing and moisturizing" lathering liquid to provide a cleansing system which is better lathering, milder and more effective than the prior art kits.

OBJECT OF THE INVENTION

One object of this invention is to provide a personal cleansing kit which cleans, lathers well, conditions and moisturizes the skin.

Another object of this invention is to provide an improved cleansing system which cleans the skin with lather and which moisturizes the skin in a single washing and rinsing step.

A further object is to provide an improved method of using a liquid cleansing and moisturizing cleanser system.

It is a further object of the present invention to provide a cleansing system which is milder to the skin with improved lather vs. the prior art.

These and other objects of the present invention will become obvious from the detailed description which follows.

SUMMARY OF THE INVENTION

This invention relates to an ultra-mild, good lathering cleansing system and kit for cleansing the skin comprising a personal cleansing implement having a Lathering Factor (A) of at least about 1.1 and a mild lathering cleansing and moisturizing liquid cleansing composition suitable for cleansing the skin with good lather and at the same time moisturizing of the skin in bath or shower.

The personal cleansing implement and the cleansing and moisturizing liquid cleanser are packaged together as in a kit or system. The liquid cleanser is preferably contained in its own container within the kit.

Figure 2:
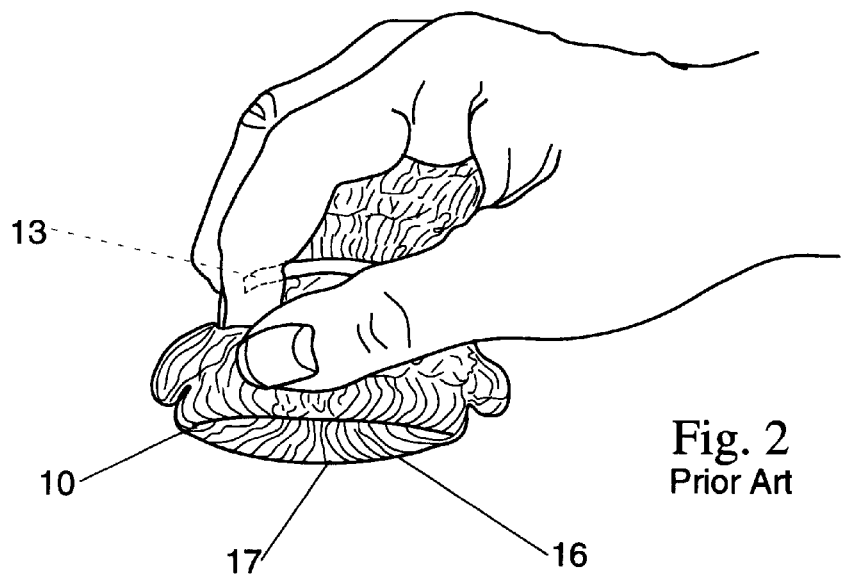
FIG. 2 is a perspective view of another hand held bath polymeric mesh sponge illustrating how it can be held in the hand.

The ease with which a cleaning polymeric mesh sponge can be held in the hand for cleaning is shown in FIG. 2. A security band 13 holds the multi-layered netting mesh together to form the polymeric mesh sponge.

Figure 3:
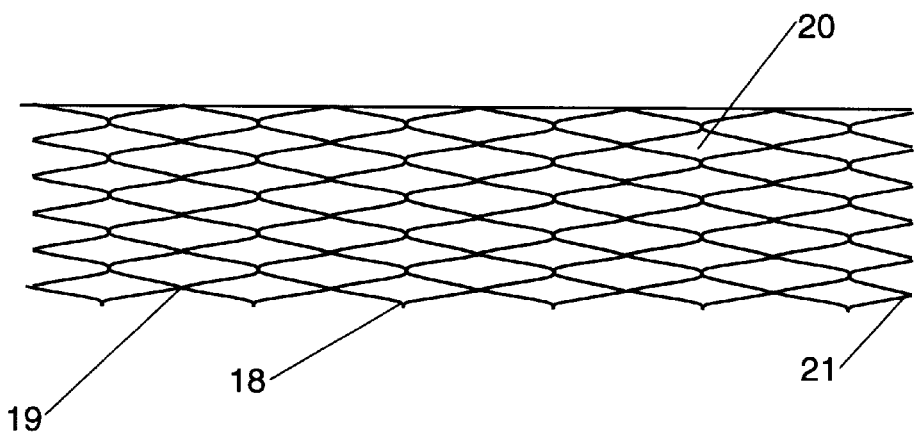
FIG. 3 is an enlarged fragmentary cross section illustrating a single sheet of a polymeric netting mesh stretched perpendicular to the filaments to show the bonding of the filaments and a representative spacing of the bonds.

The netting mesh that can be used in making the polymeric mesh sponge is illustrated in FIG. 3 wherein 21 represents the mesh in stretched position. The fire polymeric filaments used in making the netting are represented by 18 with 19 representing the spot bonding of the filaments to form the open mesh 20.

DETAILED DESCRIPTION OF THE INVENTION

The Personal Cleansing System

This invention is a kit or system that includes a personal cleansing implement and a cleansing and moisturizing liquid cleansing composition. The system is used for cleansing the skin with a mild liquid cleanser with good lather while "conditioning" or "moisturizing" the skin as it cleans in the bath or shower. The need to use a separate lotion or oil on the skin after the bath or shower is greatly reduced. Thus, the liquid is called a "cleansing and moisturizing" cleanser and the package with the personal cleansing implement is called herein a mild lathering cleansing and moisturizing personal cleansing kit. The personal cleansing implement and the cleansing and moisturizing cleanser are packaged together in a kit.

The liquid cleanser is usually contained in a separate container in an amount large enough for several uses with the mesh sponge.

The personal bath or shower body cleansing system comprising:

(A) a personal cleansing implement having a Lathering Factor(A) of at least about 1.1 as measured by the Lather Volume test set forth hereinafter in the Analytical Methods section; and (B) a liquid cleanser having: (1) an effective amount of a skin conditioning and moisturizing ingredient; and (2) an effective amount of a surfactant selected from soap and synthetic surfactants and mixtures thereof, preferably the skin conditioning and moisturizing ingredient is selected from the group consisting of oils, cationic and nonionic polymers, and mixtures thereof; and said surfactant selected from mild soaps and mild synthetic surfactants and mixtures thereof, and preferably said cleansing and moisturizing liquid cleanser (1) also contains from about 0.5% to about 10% by weight of said liquid cleanser of a skin conditioner selected from the group consisting of esters of fatty acids; glycerin mono-, di-, and trimesters; epidermal and sebaceous hydrocarbons such as cholesterol, cholesterol esters, squalene, squalane; lanolin and derivatives; mineral oil, silicone oil, silicone gum, and vegetable oil, and mixtures thereof; and preferably said liquid cleanser contains from about 0.7% to about 4% of an emulsified petrolatum which has a melting point of from about 50° C. to about 60° C.

The Personal Cleansing Implement and the Cleansing and Moisturizing Liquid Cleanser The personal cleansing implement and the otherwise low lathering cleansing and moisturizing liquid cleanser together provide a superior cleansing skin care system vs. the prior art. The cleansing and moisturizing (2-in-1) liquid cleanser provides "moisturization" via deposition of a oily material in the 2-in-1 liquid cleanser on the skin surface which material is known to improve skin condition and at a level that surpasses the threshold for a noticeable benefit. It has now been discovered that this can be accomplished by the present invention.

It has been found that this cleaning system, comprising a personal cleansing implement having a Lathering Factor (A) of at least about 1.1 used in combination with a cleansing and moisturizing liquid cleanser, provides many unexpected advantages over the prior known systems. The present system for example possesses the ability to provide both excellent lathering cleaning action and skin conditioning action in one step, so it is not necessary to utilize two separate products for both such actions. These special advantages allow the system to be mild with unexpectedly excellent lather vs. the known prior art cleansing kits. The present mild cleansing and moisturizing liquid cleanser with the personal cleansing implement herein is superior to the same cleansing and moisturizing liquid cleanser used with a regular sponge in terms of lather as well as over all acceptability by a majority of experimental users.

As hereinbefore described, the personal cleansing implements used in the present invention have a Lather Factor(A) of at least about 1.1, preferably at least about 1.2, more preferably at least about 1.5, and most preferably at least about 2.0 when used in combination with the cleansing and moisturizing compositions herein, as measured by the Lather Volume Test hereinafter set forth in the Analytical Methods section. The personal cleansing implements used in the present invention further have a Lather Factor(B) of at least about 0.8, preferably at least about 0.9, more preferably at least about 1.0, and most preferably at least about 1.1 when used in combination with the cleansing and moisturizing compositions herein, as measured by the Lather Volume Test hereinafter set forth in the Analytical Methods section. It is also preferred that the personal cleansing compositions herein have a Lather Value of at least about 200 milliliters, preferably at least about 250 milliliter, more preferably at least about 300 milliliters when used in combination with the cleansing and moisturizing compositions herein, as measured by the Lather Volume Test set forth hereinafter in the Analytical methods section.

In one preferred embodiment of the present invention, the personal cleansing implement comprises a hydrophobic polymeric netted mesh bath sponge. Such a personal cleansing implement allows the cleaning solutions used in the cleaning and gentle scrubbing action to rich lather, but also permits the moisturizing materials to deposit and thereby condition the skin.

The cleaning polymeric mesh sponge can be prepared from readily available raw materials or with specially designed mesh materials. The polymeric mesh sponge is preferably prepared from extruded tubular netting mesh which has been prepared from special strong and flexible polymeric material. Extruded tubular netting mesh of this type, and particularly those prepared from polyethylene, have been used for the covering of meat and poultry and are readily available in industry.

The polymeric mesh sponge comprises a plurality of plys of an extruded tubular netting mesh prepared from a strong flexible polymer, preferably of the group consisting of addition polymers of olefin monomers, and polyamides of polycarboxylic acids and polyamines, said plys of tubular netting mesh are folded upon itself numerous times to form a soft ball-like polymeric mesh sponge.

The tubes or stripes of netted mesh polymer can be securely attached by means of a nylon band or suitable closure. This type of polymeric mesh sponge is disclosed in U.S. Pat. No. 4,462,135, Jul. 31, 1984, to Sanford, incorporated herein by reference.

An example of a hand-held ball-like polymeric mesh sponge is disclosed in U.S. Pat. No. 5,144,744, to Campagnoli, Sept. 8, 1992, incorporated herein by reference. It is a diamond-mesh polyethylene sponge obtained from a number of netting tubes stretched over supports, joined and bound together at the center and then released from the supports.

Commercially available "polymeric mesh sponges" are sold by The Body Shop and Bynum Concepts, Inc.

The following are some specifications for suitable bath polyethylene polymeric mesh sponges:

| Size Dia. | Tubes | Ea. Length | Total Length | Wt gm. |
|-----------|-------|------------|--------------|--------|
| 3" | 2 | 60 cm | 120 cm | 15 |
| 4" | 4 | 50 cm | 200 cm | 23 |
| 5" | 4 | 80 cm | 320 cm | 37 |

One (1") inch = 2.54 cm.; 3" = 3 × 2.54 = cm.; 4" = 4 × 2.54 = cm.; etc.

Figure 1:
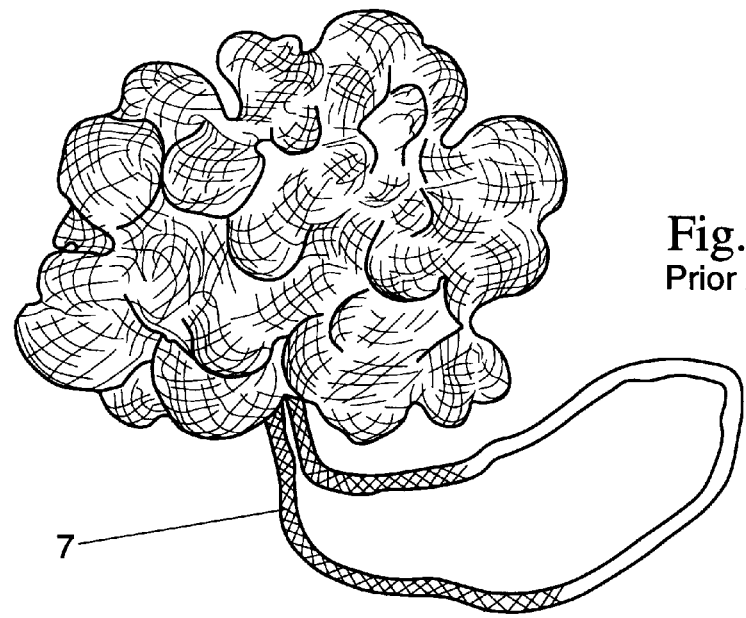
FIG. 1 is a perspective representation of a diamond-mesh polymeric hand held ball-like bath sponge showing a rope handle 7 used in the present invention.

FIG. 1 is a perspective representation of a diamond-mesh polymeric hand held ball-like bath sponge showing a rope handle 7 used in the present invention. The ease with which a cleaning polymeric mesh sponge can be held in the hand for cleaning is shown in FIG. 2. A security band 13 holds the multi-layered netting mesh together to form the polymeric mesh sponge. The netting mesh that can be used in making the polymeric mesh sponge is illustrated in FIG. 3 wherein 21 represents the mesh in stretched position. The fine polymeric filaments used in making the netting are represented by 18 with 19 representing the spot bonding of the filaments to form the open mesh 20.

Two 2 netting tubes at 60 cm length, each can be used to make a 3-inch ball sponge. They can be bundled manually with a loop or rope to form a ball-like polymeric mesh sponge. Other designs such as rectangular gloves and washings implements made with the mesh material also work very well in the system of the present invention by increasing the lather of normally lower lathering cleansing and moisturizing liquid cleansers. Some examples of such cleaning implements are the subjects of two U.S. Pat. Appl. of Girardot et at., filed Mar. 31, 1994, Ser. No. 08/221,428, now U.S. Pat. No. 5,465,452 and Ser. No. 08/221,430, now U.S. Pat. No. 5,412,830 incorporated herein by reference.

THE CLEANSING AND MOISTURIZING LIQUID CLEANSER

The term "cleansing and moisturizing liquid" or 2-in-1 liquid cleanser as used herein includes lathering liquids and semi-solid creams which contain both a lathering ingredient and a moisturizing agent.

A preferred cleansing and moisturizing personal cleansing liquid product comprises:
(a) a personal cleansing implement having a Lathering Value of at least about 250 milliliters; and
(b) a cleansing and moisturizing liquid emulsion having at least two phases, wherein said liquid emulsion comprises:
(1) a moisturizing phase comprising from about 2.0% to about 25% by weight of the liquid emulsion of a skin conditioner ingredient; and
(2) an aqueous cleansing phase comprising i) from about 5.1)% to about 20% by weight of the liquid emulsion of a lathering surfactant mixture of surfactants having an equilibrium surface tension ranging from about 15 to about 50 dynes/cm as measured at the critical micelle concentration at 25° C.; and ii) water.

A preferred cleansing and moisturizing personal cleansing liquid product comprises: (a) from about 0.1% to about 20% of anionic surfactant; (b) from about 0.1% to about 20% of amphoteric surfactant; (c) from about 0.5% to about 25% of a vegetable oil adduct, minors and; (d) balance water.

The anionic surfactant and amphoteric surfactant together can comprise from about 0.5% to about 30% by weight of the composition; a preferred weight ratio of anionic surfactant:amphoteric surfactant is in the range from about 1:5 to about 20:1.

A preferred vegetable oil adduct can be made by Diels-Alder addition of a conjugated, elaidinized form of the vegetable oil with acrylic acid, fumaric acid or maleic anhydride. The preferred adduct is maleated soybean oil. The compositions provide excellent-in-use and efficacy benefits including cleansing and lathering as well as improved mildness and skin conditioning.

Another preferred cleansing and moisturizing cleansing composition can contain ingredients selected from the group consisting of: (a) 8% to 35% polyol; (b) 35% to 70%; preferably 40% to 65% water; (c) 5% to 20%, preferably 7% to 19%, of mostly insoluble saturated (low IV of zero to 15) $C_8$–$C_{22}$ fatty acid potassium soap; (d) 0.1% to 7%, preferably 0.5 to 5%, of free $C_8$–$C_{22}$ fatty acids; and (e) 0.5% to 5%, preferably 0.7% to about 4.5% petrolatum, and mixtures thereof.

The polyol is selected from the group consisting of: glycerin, glycerol, propylene glycol, polypropylene glycols, polyethylene glycols, ethyl hexanediol, hexylene glycols, and other aliphatic alcohols; and mixtures thereof. When propylene glycol is used as a moisturizer, it is used at a level of at least 5%. The polyols are preferably used at levels of from about 10–30%.

The liquid cleanser can contain from about 0.5% to about 15% of a lipophilic emollient moisturizer selected from the group consisting of: petrolatum; esters of fatty acids; glycerin mono-, di-, and tri-esters; epidermal and sebaceous hydrocarbons such as cholesterol, cholesterol esters, squalene, squalane; silicone oils and gums; mineral oil; lanolin and derivatives and the like; and mixtures thereof.

A preferred improved stable product with a moisturizing benefit is achieved with the incorporation of larger sized petrolatum particles into selected fatty acid/soap matrixes. The larger sized petrolatum particles will vary for a liquid or semi-solid. The key is to select the fatty acid and/or soap matrix as exemplified herein, and mix in the petrolatum using a minimal controlled amount of shear to maintain larger petrolatum particles and achieve a homogeneous stable product, e.g., an improved benefit is also achieved in a semi-solid cleansing cream.

Any fatty acid matter (free and neutralized) used in the liquid cleanser preferably has an Iodine Value (I.V.) of from zero to about 15, preferably below 10, more preferably below 3.

LATHERING SOAP AND/OR SYNTHETIC SURFACTANT

The personal bath or shower body cleansing system preferably comprises from about 0.5% to about 30% of lathering surfactant having a lathering grade at least as well as C16 alkyl glyceryl ether sulfonate. The preferred cleansing and moisturizing composition contains from about 1% to about 25%, preferably from about 5 to about 25%, or 10–20% of a lathering soap and/or synthetic surfactant. A preferred surfactant is selected from mild soaps and mild synthetic surfactants and mixtures thereof. Examples of these are mild soaps and surfactants are shown in the Examples herein.

The soaps are preferably those derived from essentially saturated hydrocarbon having chain lengths of from about 8 to about 22. It is preferred that the soap be the potassium salt, but other soluble soaps can be used. Some sodium, ammonium, triethanolammonium, and/or mixtures thereof, are deemed acceptable, at least in potassium blends. The soaps are preferably prepared in-situ by neutralization of the corresponding fatty acids, but they may also be introduced as preformed soaps.

The preferred liquid soap is called a dispersoid because at least some of the fatty matter at the levels used herein is insoluble. The level of water in the compositions is typically from about 35% to about 70%, preferably from about 40% to about 65%.

Another important attribute of the preferred liquid soap of the present invention is it is phase stable, particularly after storage.

An important attribute of the preferred soap personal cleansing product of the present invention is its rich and creamy lather.

An important component of liquid cleansers is a lather boosting surfactant. The surfactant, which may be selected from any of a wide variety of anionic (soaps and nonsoap), amphoteric, zwitterionic, nonionic and, in certain instances, cationic surfactants, is present at said levels.

It is noted that surfactant mildness can be measured by a skin barrier destruction test which is used to assess the irritancy potential of surfactants. In this test the milder the surfactant, the lesser the skin barrier is destroyed. Skin barrier destruction is measured by the relative amount of radio-labeled water ($^3$H—H$_2$O) which passes from the test solution through the skin epidermis into the physiological buffer contained in the diffusate chamber. This test is described by T. J. Franz in the *J. Invest. Dermatol.*, 1975, 64, pp. 190–195; and in U.S. Pat. No. 4,673,525, Small et al., issued Jun. 16, 1987, incorporated herein by reference, and which disclose a mild alkyl glyceryl ether sulfonate (AGS) surfactant based synbar comprising a "standard" alkyl glyceryl ether sulfonate mixture. Barrier destruction testing is used to select mild surfactants.

The liquid composition preferably comprises a lathering surfactant selected from the group consisting of anionic surfactants, nonionic surfactants, zwitterionic surfactants, amphoteric surfactants, and mixtures thereof.

The lathering surfactant is defined herein as a synthetic surfactant or mixes thereof that when combined have an equilibrium surface tension of between 15 and 50 dynes/cm, more preferably between 20 and 45 dynes/cm as measured at the CMC (critical micelle concentration) at 25° C. Some surfactant mixes can have surface tensions lower than of its components.

Some examples of good lather-enhancing, mild detergent surfactants are e.g., sodium or potassium lauroyl sarcosinate, alkyl glyceryl ether sulfonate, sulfonated fatty esters, and sulfonated fatty acids. Thus, a high lathering surfactant is defined herein as one which lathers on the order of C16 alkyl glyceryl ether sulfonate or better. For a lather volume test, see U.S. Pat. No. 5,264,145, to French et al., Nov. 23, 1993, incorporated herein by reference.

Numerous examples of other surfactants are disclosed in the literature: they include other alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and alkyl amine oxides, betaines, sultaines, and mixtures thereof. Included in the suifactants are the alkyl ether sulfates with 1 to 12 ethoxy groups, especially ammonium and sodium lauryl ether sulfates.

Many additional nonsoap surfactants are described in McCUTCHEON'S, DETERGENTS AND EMULSIFIERS, 1993 Edition, published by MC Publishing Co., which is incorporated here by reference.

The above-mentioned surfactants can be used in the cleansing bath/shower compositions of the present invention. The anionic surfactants, particularly the alkyl sulfates, the ethoxylated alkyl sulfates and mixtures thereof are preferred. More preferred are $C_{12}$–$C_{14}$ alkyl anionic surfactants selected from the group consisting of sodium alkyl glycerol ether sulfonate, sodium lauroyl sarcosinate, sodium alkyl sulfate, sodium ethoxy (3) alkyl sulfate, and mixtures thereof.

Nonionic surfactants can be broadly defined as compounds produced by the condensation of alkylene oxide groups (hydrophilic in nature) with an organic hydrophobic compound, which may be aliphatic or alkyl aromatic in nature.

The pH of the neat cleansing bath/shower liquid soap compositions herein is generally from about 7.0 to about 9.5, preferably from about 7.5 to about 9 as measured at 25° C. The pH of the liquid synthetic surfactant composition is about 4 to 8, preferably 4.5 to 7.

The cleansing and moisturizing liquid cleanser preferably has an apparent or neat viscosity of from about 500 cps to about 60,000 cps at 26.7° C., preferably 5,000 to 30,000 cps. The term "viscosity" as used herein means the viscosity as measured by a Brookfield RVTDCP with a spindle CP-41 at 1 RPM for 3 minutes, unless otherwise specified. The "neat" viscosity is the viscosity of the undiluted liquid cleanser.

Skin conditioner or moisturizer

Skin conditioner or moisturizer deposition from a cleansing system is measured by one of two protocols, both are modeled after how skin cleansing products are typically used by consumers. One protocol is done "in vitro", while the second is done "in vivo".

In the in vitro protocol, a model skin substrate is used which is a collagen sheet that has a surface topography similar to human skin and has been pre-hydrated. Small pieces of the substrated are mounted over flask openings to secure them for exposure to lather. The lather is generated in the palms of hands, the polymeric mesh sponge or other cleansing implement, using the following controlled procedure: one gram of product plus 3 ml of water for 10 seconds. The mounted substrate is then exposed to the combined lather by overturning the flask and rubbing it on the palm of the hand, etc. This lathering process is continued for 10 seconds and, after allowing the lather to remain on the substrate for 5 seconds, it is rinsed with warm tap water for 10 seconds. The exposed skin substrate is then cut from the mount and dried prior to analysis. The analysis procedure is to submerge the substrate in 1:1 ethanol:heptane if petrolatum is measured or another solvent for other moisturizers and then analyze this extract by standard gas chromatographic methods.

The in vivo protocol is similar to the in vitro one described above, except the lather generated in the polymeric mesh sponge (or the palm of the hand) is applied to the opposite forearm. The time that the lather remains on the forearm is 30 seconds (compared to the 5 seconds on the collagen substrate). The deposited conditioner is then extracted by strapping an open-ended glass cylinder to the forearm and adding the appropriate solvent to this cylinder. As above, the extract is then analyzed according to standard gas chromatographic methods.

The cleansing bath/shower compositions can contain a variety of nonessential optional ingredients suitable for rendering such compositions more desirable. Such conventional optional ingredients are well known to those skilled in the art, e.g., preservatives such as benzyl alcohol, methyl paraben, propyl paraben and imidazolidinyl urea; other thickeners and viscosity modifiers such as $C_8$–$C_{18}$ ethanolamide (e.g., coconut ethartolamide); pH adjusting agents such as citric acid, succinic acid, phosphoric acid, sodium hydroxide, etc.; suspending agents such as magnesium/ aluminum silicate; perfumes; dyes; and sequestering agents such as disodium ethylenediamine tetraacetate.

If present, the optional components individually generally comprise from about 0.001% to about 10% by weight of the composition, but can be more or less.

Optional thickeners are categorized as cationic, nonionic, or anionic and are selected to provide the desired viscosity. Suitable thickeners are listed in the Glossary and Chapters 3, 4, 12 and 13 of the *Handbook of Water-Soluble Gums and Resins,* Robert L. Davidson, McGraw-Hill Book Co., New York, N.Y., 1980, incorporated by reference herein.

The liquid personal cleansing products can be thickened by using polymeric additives that hydrate, swell or molecularly associate to provide body (e.g., hydroxypropyl guar gum is used as a thickening aid in shampoo compositions).

A suitable thickener is hydroxy ethyl cellulose, e.g., NatrosolR 250 KR sold by The Aqualon Company.

Another thickener is acrylated steareth-20 methylacrylate copolymer sold as Acrysol ICS-1 by Rohm and Haas Company.

The amount of polymeric thickener found useful in the present compositions is about 0.1% to about 2%, preferably from about 0.2% to about 1.0%.

The liquid cleanser can be made with from about 0.1% to about 5%, preferably from about 0.3% to about 3%, of a skin moisturizing cationic polymer selected from the group consisting of: cationic polysaccharides and derivatives, cationic copolymers of saccharides and synthetic monomers, synthetic copolymers and cationic protein derivatives.

MAKING A SOAP-BASED CLEANSING AND MOISTURIZING LIQUID CLEANSER

Most methods of making cleansing and moisturizing liquid cleansers for the present invention use standard industry equipment. For example, a general process for a 6000 gram size batch using a 4.5 gallon jacketed tank agitated by a Lightning Mixer (Model TS2010) fitted with a three prong propeller size agitator with blades measuring one inch. However, mixing times will vary with equipment, batch size, etc.

1. The fatty acids (the oil phase), antimicrobial (if added), etc. is added to a sanitary agitated and jacketed stainless steel vessel;
2. The oil phase is heated to about 80° C.
3. Polyol liquids (e.g., propylene glycol) and some surfactant are added to the heated oil phase.
4. In a separate container, a water phase is prepared containing polymers, polyol liquids (e.g., glycerin), and water, and heated to 80° C. with agitation.
5. The appropriate base (e.g., potassium hydroxide) for an in situ soap formation is added and mixed into the oil phase.
6. Next, the water phase is added and mixed to the oil phase/soap vessel.
7. Glycol ester is melted and mixed into (6) at about 80° C.
8. Any additional surfactant is added to (7) at about 80° C.
9. The product of (8) is cooled to about 45° C. at which time other minors such as preservatives and perfumes can be added.
10. The conditioner, e.g., petrolatum is added and mixed to (9) at a temperature of between about 35° C. to about 45° C. or about or at a temperature below its melting point.

Alternatively, the product of Step 9 may stand prior to adding materials such as petrolatum. In case of the product standing, the product of Step 9 is reheated to about 35° C., before the petrolatum is added.

In the method of making the product of this invention, the large petrolatum particle size is controlled by mix time and addition temperature. The shorter the mix time and the lower the temperature, the higher the proportion of larger petrolatum emollient particles is achieved.

A preferred allowed mild liquid personal cleanser is disclosed in allowed U.S. patent application Ser. No. 07/909, 834, filed Jul. 7, 1992, Dias, et al., now U.S. Pat. No. 5,308,526, incorporated herein by reference.

The cleansing bath/shower compositions can contain a variety of nonessential optional ingredients suitable for rendering such compositions more desirable. Such conventional optional ingredients are well known to those skilled in the art, e.g., preservatives such as benzyl alcohol, methyl paraben, propyl paraben and imidazolidinyl urea; other thickeners and viscosity modifiers such as $C_8$–$C_{18}$ ethanolamide (e.g., coconut ethanolamide); pH adjusting agents such as citric acid, succinic acid, phosphoric acid, sodium hydroxide, etc.; suspending agents such as magnesium/ aluminum silicate; perfumes; dyes; and sequestering agents such as disodium ethylenediamine tetraacetate.

MAKING A PREFERRED CLEANSING AND MOISTURIZING LIQUID CLEANSER

This method comprises the following steps:

a) Forming an aqueous phase comprising from about 0.1% to about 50% by weight of final composition of surfactant;

b) Forming a first oil phase comprising from about 0.5% to about 10% by weight of final composition of nonionic emollient oil or wax other than the vegetable oil adduct;

c) Forming a second oil phase comprising from about 0.5% to about 25%, preferably from about 0.5% to about 15% by weight of final composition of the vegetable oil adduct;

d) Premixing the first oil phase and the aqueous surfactant phase to form an emulsion of the first oil phase in water; and e) Thereafter admixing the second oil phase with the oil-in-water emulsion of step (d), thereby forming an emulsion of the second oil phase in the preformed oil-in-water emulsion of the first oil phase.

The following personal bath or shower body cleanser kit is highly preferred one. The preferred 2-in-1 liquid cleanser comprises:

| Ingredients in parts by wt. of the liquid cleanser: | from | to |
|---|---|---|
| Water | 55 | 60 |
| Cocoamphoacetate/ Cocoamphodiacetate | 4 | 8 |
| Sodium Laureth-3 Sulfate | 10 | 15 |
| Alkylpolysaccharide | 0 | 3 |
| Coconut monoethanol amide | 2 | 3 |
| Soybean Oil | 7 | 9 |
| Maleated Soybean Oil | 1 | 4 |
| Polymer JR30 | 0.2 | 0.6 |
| PEG(6) Caprylic/ Caprylglycerate | 3 | 5 |

-continued

| Ingredients in parts by wt. of the liquid cleanser: | from | to |
|---|---|---|
| Myristic Acid | 0 | 3 |
| Palm Kernel Acid | 2 | 0 |
| Glycerine | 2 | 4 |
| Titanium Dioxide | 0 | 0.2 |
| Perfume | 1 | 2 |
| Preservative | 0.1 | 0.3 |

This liquid cleanser with moisturizer is contained in a separate dispenser for periodic dispensing a portion of the 2-in-1 cleanser onto a mesh sponge as shown in FIG. 1 for use in bath or shower.

ANALYTICAL METHODS

Equipment
  Beaker (800 mL)
  Hot Plate with stirrer
  Water Hardness Kit (if performing test with 14 grain water)
  Rubbermaid Bath Mat
Method:
1. Prepare 700 ml of 14 grain water
2. Using a hot plate and stirrer, bring water temperature to a uniform 95° F.
3. Weigh dry implement. Submerge implement for 5 seconds in water.
4. Remove implement from water, suspend implement for 3 seconds and then squeeze at firmly at center of implement with one hand for 3 seconds to eliminate excess water.
5. Place implement on rubber testing surface (Rubbermaid Bath Mat) and add 2 mLs of product to face of implement.
6. Rub hand six times up and down the face of the implement to spread product over implement (1 up and 1 down equals one time).
7. Place implement on rubber testing surface with the surface with product facing down.
8. Using a controlled amount of compression and stroke length (18 inches) rub sponge back and forth. Each back and forth motion should take one second. Repeat the motion 60 times (1 minute.)
9. Collect lather using a Teflon spatula and place lather in 800 ml beaker. Level lather and measure in milliliters. (Lather volume=Lather Value)
10. Repeat steps 1–9 using a uniform, synthetic sponge having the following parameters:
   Thickness: 1.88 inches
   Surface Area: 17.81 inches
   Volume: 33.40 inches
   Weight: 9.7 grams
11. Repeat steps 1–9 using an Oil of Olay Body Puff
Calculations:

$$\text{Lather Factor (A)} = \frac{\text{Lather volume}_{implement}}{\text{Lather volume}_{sponge}}$$

$$\text{Lather Factor (B)} = \frac{\text{Lather volume}_{implement}}{\text{Lather volume}_{puff}}$$

EXAMPLES

The following examples of cleansing and moisturizing liquid cleansers and the specific meshed sponges are illustrative and are not intended to limit the scope of the invention(s). The preferred method of making the cleansing and moisturizing liquid cleansing compositions of the present invention is set out above. All levels, ranges, temperatures, results, etc., used herein are approximations, unless otherwise specified. All formula percentages are expressed as a weight percentage of the liquid cleanser unless otherwise specified.

EXAMPLES 1–6

Examples 1–6 are cleansing and moisturizing liquid Compositions which demonstrate varying levels and types of conditioner(s) and varying levels of soap and/or surfactant. Example 6 is a highly preferred cleansing and moisturizing liquid cleanser. A polyethylene-meshed hand held sponge as shown in FIG. 1 is a preferred polymeric mesh sponge for the present system.

| EXAMPLES | 1 | 2 | 3 | 4 |
|---|---|---|---|---|
| Ingredients: | | | | |
| Water | 42.36 | 49.0 | 40.6 | 49.0 |
| Stearic Acid | 0.67 | 0.22 | 0.67 | 0.22 |
| Palmitic Acid | 1.13 | 0.38 | 1.13 | 0.38 |
| Myristic Acid | 1.35 | 0.45 | 1.35 | 0.45 |
| Lauric Acid | 1.35 | 0.45 | 1.35 | 0.45 |
| In Situ potassium soap | 15.0 | 17.0 | 11.0 | 17.0 |
| Glycerin | 15.0 | 15.0 | 15.0 | 15.0 |
| Propylene Glycol | 10.0 | 7.0 | 10.0 | 7.0 |
| $Na_5$Pentetate | 0.02 | 0.02 | 0.02 | 0.02 |
| $Na_4$Etidronate | 0.02 | 0.02 | 0.02 | 0.02 |
| Sodium Lauroyl Sarcosinate | 6.0 | 6.0 | 6.0 | 6.0 |
| Sodium Laureth Sulfate | 0.67 | — | 2.0 | — |
| CocoAmido Propyl Betaine | 1.33 | 1.33 | 4.0 | — |
| Cetyl Ricinoleate | — | — | — | 0.75 |
| Polyquaternium-10 | 0.8 | 0.6 | 1.0 | 0.6 |
| Fragrance | 0.5 | 0.6 | 0.6 | 0.6 |
| Ethyleneglycol Distearate | 1.5 | 1.0 | 1.5 | 1.0 |
| Preservatives | 0.8 | 0.8 | 0.8 | 0.8 |
| Petrolatum | 1.5 | 1.5 | 3.0 | 0.75 |

The stable liquid cleansers of Examples 1–4 are prepared in accordance with a method set out above. Care is taken to add the petrolatum in Step 10 at a temperature below its melting point (MP), using gentle mixing to ensure large petrolatum particles, preferably having weight average sizes over 45 microns.

| EXAMPLES | 5 | 6 |
|---|---|---|
| Ingredients: | | |
| Water | 57.9 | 55.70 |
| Cocoamphoacetate/Cocoamphodiacetate | 6.0 | 6.0 |
| Sodium Laureth-3 Sulfate | 12.0 | 12.0 |
| Alkylpolysaccharide | 0.00 | 2.00 |
| Coconut monoethanol amide | 2.80 | 2.80 |
| Soybean Oil | 8.00 | 8.00 |
| Maleated Soybean Oil | 2.00 | 2.00 |
| Polymer JR30 | 0.40 | 0.40 |
| PEG(6) Caprylic/Caprylglycerate | 4.00 | 4.00 |
| Myristic Acid | 0.00 | 2.00 |
| Palm Kernel Acid | 1.80 | 0.00 |
| Glycerine | 3.00 | 3.00 |
| Titanium Dioxide | 0.10 | 0.10 |

-continued

| EXAMPLES | 5 | 6 |
|---|---|---|
| Perfume | 1.80 | 1.80 |
| Preservative | 0.20 | 0.20 |

MILDNESS AND LATHER RESULTS

The Mildness Protocol. Human subjects precondition their legs with an all soap bar by washing twice a day for seven days. Treatments are applied daily for 5 consecutive days. On each day, skin dryness grades can be taken before treatment (to measure chronic effects) and 60 minutes after treatment (measure acute effects).

On each day of the test, three 12.5 $cm^2$ sites are treated on each of the subjects. Three treatments are assigned using a Latin square design, which takes into account baseline site-to-site differences in skin condition within each subject. The treatments are:

I. A mild syndet bar.

II. A mild syndet bar plus a moisturizing lotion applied after washing.

III. A cleansing and moisturizing liquid cleanser, Example 6, used with a polymeric mesh sponge as shown in FIG. 1.

IV. A cleansing and moisturizing liquid cleanser, Example 6, used with a regular closed-cell sponge.

MILDNESS RESULTS

Treatment III represents the "System" of the present invention. Treatment III is the 2-in-1 liquid cleanser Example 6 used with a "polymeric mesh sponge" as show in FIG. 1.

Treatment II is a mild syndet bar plus a lotion. It is a very mild treatment because the lotion is applied directly to the skin after washing. This is not a 2-in-1 cleansing and moisturizing treatment, but is used as a control. Note, however, that many people do not use a moisturizer after bathing or showering. The 2-in-1 cleanser is always milder than the mild syndet bar alone.

Treatment III, the 2-in-1 liquid cleanser, Example 6, used with the mesh sponge, is significantly milder than the mild syndet bar alone, i.e., without the lotion in chronic mildness and equal to it in acute mildness.

Treatment III has improved overall acceptability over Treatment IV, the cleansing and moisturizing liquid cleanser, Example 6, used with a regular sponge. See for example the comparative lather results below.

LATHER TEST PROTOCOL FOR MESH SPONGE VS. REGULAR SPONGE SYSTEMS

Expert lather graders are asked to successively lather a 2-in-1 formula (Example 6 ) with the mesh sponge (FIG. 1) and with a regular closed-cell sponge. The order is randomized. The expert lather graders are asked to rate the two systems for lather on a −3/+3 scale.

1. Start test on left forearm with sponge A (or B).

2. Wet cleansing sponge for 5 seconds under 95 degree running water.

3. Put one pump of product (3 cc) on to the wet sponge.

4. Squeeze sponge 10 times using both hands to generate lather.

5. Wet forearm under running water.

6. Lather forearm with sponge using an up and down motion for 10 seconds.

7. Evaluate the lather on forearm using a −3 to +3 scale.

8. Repeat entire procedure on right arm with sponge B (or A).

LATHER RESULTS

The results shown in the Table indicate that the 2-in-1 formula (Example 6) lathers more quickly and produces more lather when used in combination with the mesh sponge than it does with a regular closed-cell sponge.

| Lather Results Table | | |
|---|---|---|
| | Regular Sponge | Mesh Sponge |
| Lather Quickly/Easily | −0.80 | +2.50 |
| Amount of Lather | −0.79 | +2.25 |

The system of the present invention has improved lather grades as shown in the Lather Results Table. The significance is calculated at 95% confidence. In other words, the 2-in-1 liquid cleanser used with a meshed polymeric mesh sponge has unexpected and superior lather and overall acceptability over the 2-in-1 liquid cleanser used with a regular sponge.

The present system of cleansing body skin using a cleansing and moisturizing liquid cleanser and the polymeric mesh sponge has improved lather and overall unexpected and surprising advantages over prior art systems.

What is claimed is:

1. A personal bath or shower body cleansing and lathering product comprising:
    (a) a personal cleansing implement having a Lathering Factor (A) of at least about 1.1; and
    (b) a cleansing and moisturizing liquid emulsion having at least two phases, wherein said liquid emulsion comprises:
        (1) a moisturizing phase comprising from about 0.5% to about 33.5% by weight of the liquid emulsion of a skin conditioner ingredient; and
        (2) an aqueous cleansing phase comprising i) from about 0.5% to about 30% by weight of the liquid emulsion of a lathering surfactant or mixture of surfactants having an equilibrium surface tension ranging from about 15 to about 50 dynes/cm as measured at the critical micelle concentration at 25° C.; and ii) water.

2. A personal bath or shower body cleansing and lathering product according to claim 1 wherein the skin conditioner ingredient is selected from the group consisting of esters of fatty acids, glycerin mono-esters, glycerin di-esters, glycerin tri-esters, epidermal and sebaceous hydrocarbons, lanolin, mineral oil, silicone oil, silicone gum, vegetable oil, petrolatum, vegetable oil adduct, cationic polymers and mixtures thereof.

3. A personal bath or shower body cleansing and lathering product according to claim 2 wherein the lathering surfactant is selected from the group consisting of anionic surfactants and mixtures of anionic surfactants with amphoteric surfactants, zwitterionic surfactants, nonionic surfactants, cationic surfactants and mixtures thereof.

4. A personal bath or shower body cleansing and lathering product according to claim 3 comprising a kit, wherein said kit comprises the personal cleansing implement and the cleansing and moisturizing liquid emulsion.

5. The personal bath or shower body cleansing and lathering kit of claim 4 wherein the cleansing and moisturizing liquid emulsion comprises from 0.5% to 25% by weight of the skin conditioner ingredient within the moisturizing phase.

6. The personal bath or shower body cleansing and lathering kit of claim 5 wherein said cleansing and moisturizing liquid emulsion has a neat viscosity of from about 500 cps to about 60,000 cps at 26.7° C.

7. The personal bath or shower body cleansing and lathering kit of claim 6 wherein the cleansing and moisturizing liquid emulsion additionally comprises a skin conditioner ingredient within the aqueous cleansing phase, wherein the skin conditioner ingredient within the aqueous phase includes ingredients selected from the group consisting of cationic and nonionic polymers, polyols selected from the group consisting of glycerin, propylene glycol, polypropylene glycols, polyethylene glycols, ethyl hexanediol, hexylene glycols, and mixtures thereof.

8. The personal bath or shower body cleansing and lathering kit of claim 7 wherein the lathering surfactant comprises from about 0.1% to about 20% by weight of anionic surfactant and from about 0.1% to about 20% by weight of amphoteric surfactant; wherein the anionic surfactant and amphoteric surfactant together comprise from about 0.5% to about 30% by weight of the emulsion; and wherein the weight ratio of anionic surfactant amphoteric surfactant ranges from about 1:5 to about 20:1.

9. The personal bath or shower body cleansing and lathering kit of claim 8 wherein the emulsion is selected from the group consisting of oil-in-water emulsions, silicone-in-water emulsions, and mixtures thereof.

10. The personal bath or shower body cleansing and lathering kit of claim 9 wherein the skin conditioner ingredient within the moisturizing phase of said cleansing and moisturizing liquid emulsion comprises a skin conditioner selected from the group consisting of petrolatum, vegetable oil, vegetable oil adduct and mixtures thereof.

11. A personal bath or shower body cleansing and lathering kit of claim 10 wherein the personal cleansing implement has a Lathering Factor (A) of at least about 1.5.

12. A personal bath or shower body cleansing and lathering product according to claim 3 wherein the cleansing and moisturizing liquid emulsion is combined with the personal cleansing implement.

13. The personal bath or shower body cleansing and lathering product of claim 12 wherein the cleansing and moisturizing liquid emulsion comprises from 0.5% to 25% by weight of the skin conditioner ingredient within the moisturizing phase.

14. The personal bath or shower body cleansing and lathering product of claim 13 wherein said cleansing and moisturizing liquid emulsion has a neat viscosity of from about 500 cps to about 60,000 cps at 26.7° C.

15. The personal bath or shower body cleansing and lathering product of claim 14 wherein the cleansing and moisturizing liquid emulsion additionally comprises a skin conditioner ingredient within the aqueous cleansing phase, wherein the skin conditioner ingredient within the aqueous phase includes ingredients selected from the group consisting of cationic and nonionic polymers, polyols selected from the group consisting of glycerin, propylene glycol, polypropylene glycols, polyethylene glycols, ethyl hexanediol, hexylene glycols, and mixtures thereof.

16. The personal bath or shower body cleansing and lathering product of claim 15 wherein the lathering surfactant comprises from about 0.1% to about 20% by weight of anionic surfactant and from about 0.1% to about 20% by weight of amphoteric surfactant; wherein the anionic surfactant and amphoteric surfactant together comprise from about 0.5% to about 30% by weight of the emulsion; and wherein the weight ratio of anionic surfactant amphoteric surfactant ranges from about 1:5 to about 20:1.

17. The personal bath or shower body cleansing and lathering product of claim 16 wherein the emulsion is selected from the group consisting of oil-in-water emulsions, silicone-in-water emulsions, and mixtures thereof.

18. The personal bath or shower body cleansing and lathering product of claim 17 wherein the skin conditioner ingredient within the moisturizing phase of said cleansing and moisturizing liquid emulsion comprises a skin conditioner selected from the group consisting of petrolatum, vegetable oil, vegetable oil adduct and mixtures thereof.

19. A personal bath or shower body cleansing and lathering product of claim 18 wherein the personal cleansing implement has a Lathering Factor (A) of at least about 2.0.

20. A personal bath or shower body cleansing and lathering product comprising:
(a) a personal cleansing implement having a Lathering Value of at least about 250 milliliters; and
(b) a cleansing and moisturizing liquid emulsion having at least two phases, wherein said liquid emulsion comprises:
(1) a moisturizing phase comprising from about 2.0% to about 25% by weight of the liquid emulsion of a skin conditioner ingredient; and
(2) an aqueous cleansing phase comprising i) from about 5.0% to about 20% by weight of the liquid emulsion of a lathering surfactant or mixture of surfactants having an equilibrium surface tension ranging from about 15 to about 50 dynes/cm as measured at the critical micelle concentration at 25° C.; and ii) water.

21. A personal bath or shower body cleansing and lathering product according to claim 20 wherein the skin conditioner ingredient is selected from the group consisting of esters of fatty acids, glycerin mono-esters, glycerin di-esters, glycerin tri-esters, epidermal and sebaceous hydrocarbons, lanolin, mineral oil, silicone oil, silicone gum, vegetable oil, petrolatum, vegetable oil adduct, cationic polymers and mixtures thereof.

22. A personal bath or shower body cleansing and lathering product according to claim 21 wherein the lathering surfactant is selected from the group consisting of anionic surfactants and mixtures of anionic surfactants with amphoteric surfactants, zwitterionic surfactants, nonionic surfactants, cationic surfactants and mixtures thereof.

23. A personal bath or shower body cleansing and lathering product according to claim 22 comprising a kit, wherein said kit comprises the personal cleansing implement and the cleansing and moisturizing liquid emulsion.

24. The personal bath or shower body cleansing and lathering kit of claim 23 wherein said cleansing and moisturizing liquid emulsion has a neat viscosity of from about 500 cps to about 60,000 cps at 26.7° C.

25. The personal bath or shower body cleansing and lathering kit of claim 24 wherein the cleansing and moisturizing liquid emulsion additionally comprises a skin conditioner ingredient within the aqueous cleansing phase, wherein the skin conditioner ingredient within the aqueous phase includes ingredients selected from the group consisting of cationic and nonionic polymers, polyols selected from the group consisting of glycerin, propylene glycol, polypropylene glycols, polyethylene glycols, ethyl hexanediol, hexylene glycols, and mixtures thereof.

26. The personal bath or shower body cleansing and lathering kit of claim 25 wherein the emulsion is selected from the group consisting of oil-in-water emulsions, silicone-in-water emulsions, and mixtures thereof.

27. The personal bath or shower body cleansing and lathering kit of claim 26 wherein the skin conditioner ingredient within the moisturizing phase of said cleansing and moisturizing liquid emulsion comprises a skin conditioner selected from the group consisting of petrolatum, vegetable oil, vegetable oil adduct and mixtures thereof.

28. A personal bath or shower body cleansing and lathering kit of claim 27 wherein the personal cleansing implement has a Lathering Value of at least about 300 milliliters.

29. A personal bath or shower body cleansing and lathering product according to claim 22 wherein the cleansing and moisturizing liquid emulsion is combined with the personal cleansing implement.

30. The personal bath or shower body cleansing and lathering product of claim 29 wherein said cleansing and moisturizing liquid emulsion has a neat viscosity of from about 500 cps to about 60,000 cps at 26.7° C.

31. The personal bath or shower body cleansing and lathering product of claim 30 wherein the cleansing and moisturizing liquid emulsion additionally comprises a skin conditioner ingredient within the aqueous cleansing phase, wherein the skin conditioner ingredient within the aqueous phase includes ingredients selected from the group consisting of cationic and nonionic polymers, polyols selected from the group consisting of glycerin, propylene glycol, polypropylene glycols, polyethylene glycols, ethyl hexanediol, hexylene glycols, and mixtures thereof.

32. The personal bath or shower body cleansing and lathering product of claim 31 wherein the emulsion is selected from the group consisting of oil-in-water emulsions, silicone-in-water emulsions, and mixtures thereof.

33. The personal bath or shower body cleansing and lathering product of claim 32 wherein the skin conditioner ingredient within the moisturizing phase of said cleansing and moisturizing liquid emulsion comprises a skin conditioner selected from the group consisting of petrolatum, vegetable oil, vegetable oil adduct and mixtures thereof.

34. A method of cleaning and moisturizing the skin comprising applying a cleansing and moisturizing liquid emulsion to the skin and using a personal cleansing implement having a Lathering Factor (A) of at least about 1.1 to create a lather; wherein said cleansing and moisturizing liquid emulsion has at least two phases comprising: (1) a moisturizing phase comprising from about 0.5% to about 33.5% by weight of the liquid emulsion of a skin conditioner ingredient selected from the group consisting of esters of fatty acids, glycerin mono-esters, glycerin di-esters, glycerin tri-esters, epidermal and sebaceous hydrocarbons, lanolin, mineral oil, silicone oil, silicone gum, vegetable oil, petrolatum, vegetable oil adduct, cationic polymer and mixtures thereof; and (2) an aqueous cleansing phase comprising: i) from about 0.5% to about 30% by weight of the liquid emulsion of a lathering surfactant selected from the group consisting of anionic surfactants and mixtures of anionic surfactants; wherein the surfactant or mixture of surfactants has an equilibrium surface tension ranging from about 15 to about 50 dynes/cm as measured at the critical micelle concentration at 25° C.; and ii) water.

35. A method of cleaning and moisturizing the skin comprising applying a cleansing and moisturizing liquid emulsion to the skin and using a personal cleansing implement having a Lathering Value of at least about 250 milliliters to create a lather; wherein said cleansing and moisturizing liquid emulsion has at least two phases comprising: (1) a moisturizing phase comprising from about 2.0% to about 25% by weight of the liquid emulsion of a skin conditioner ingredient selected from the group consisting of esters of fatty acids, glycerin mono-esters, glycerin di-esters, glycerin tri-esters, epidermal and sebaceous hydrocarbons, lanolin, mineral oil, silicone oil, silicone gum, vegetable oil, petrolatum, vegetable oil adduct, cationic polymer and mixtures thereof; and (2) an aqueous cleansing phase comprising: i) from about 5% to about 20% by weight of the liquid emulsion of a lathering surfactant selected from the group consisting of anionic surfactants and mixtures of anionic surfactants; wherein the surfactant or mixture of surfactants has an equilibrium surface tension ranging from about 15 to about 50 dynes/cm as measured at the critical micelle concentration at 25° C.; and ii) water.

36. A method of cleansing and moisturizing the skin comprising applying a cleansing and moisturizing liquid emulsion to a personal cleansing implement having a Lathering Factor (A) of at least about 1.1, working the cleansing and moisturizing liquid emulsion into a lather, and applying the lathered emulsion to the skin with the personal cleansing implement; wherein said cleansing and moisturizing liquid emulsion has at least two phases comprising: (1) a moisturizing phase comprising from about 0.5% to about 33.5% by weight of the emulsion of a skin conditioner ingredient selected from the group consisting of esters of fatty acids, glycerin mono-esters, glycerin di-esters, glycerin tri-esters, epidermal and sebaceous hydrocarbons, lanolin, mineral oil, silicone oil, silicone gum, vegetable oil, petrolatum, vegetable oil adduct, cationic polymer and mixtures thereof, and (2) an aqueous cleansing phase comprising: i) from about 0.5% to about 30% by weight of the emulsion of a lathering surfactant selected from the group consisting of anionic surfactants and mixtures of anionic surfactants; wherein the surfactant or mixture of surfactants has an equilibrium surface tension ranging from about 15 to about 50 dynes/cm, as measured at the critical micelle concentration at 25° C.; and ii) water.

* * * * *